(12) United States Patent
Kimball et al.

(10) Patent No.: US 7,198,756 B2
(45) Date of Patent: Apr. 3, 2007

(54) NON-INVASIVE MEASUREMENT OF PH

(75) Inventors: Victor E. Kimball, Burnsville, MN (US); Steven C. Furlong, Maple Grove, MN (US); Irvin Pierskalla, Prior Lake, MN (US)

(73) Assignee: Optical Sensors Incorporated, Eden Prairie, MN (US)

( * ) Notice: Subject to any disclaimer, the term of this patent is extended or adjusted under 35 U.S.C. 154(b) by 409 days.

(21) Appl. No.: 10/195,004

(22) Filed: Jul. 11, 2002

(65) Prior Publication Data
US 2004/0009606 A1 Jan. 15, 2004

(51) Int. Cl.
*G01N 33/00* (2006.01)

(52) U.S. Cl. .................. 422/82.08; 436/163; 436/164; 422/50; 422/68.1; 422/82.05; 422/82.09

(58) Field of Classification Search ................ 436/163, 436/164; 422/50, 68.1, 82.05, 82.08, 82.09
See application file for complete search history.

(56) References Cited

U.S. PATENT DOCUMENTS

| 4,200,100 | A |   | 4/1980 | Willis |
|---|---|---|---|---|
| 5,039,492 | A |   | 8/1991 | Saaski et al. |
| 5,093,266 | A |   | 3/1992 | Leader et al. |
| 5,308,581 | A |   | 5/1994 | Lippitsch et al. |
| 5,393,514 | A |   | 2/1995 | Pitner et al. |
| 5,456,252 | A |   | 10/1995 | Vari et al. |
| 5,536,783 | A |   | 7/1996 | Olstein et al. |
| 5,567,624 | A |   | 10/1996 | Smith |
| 5,607,644 | A |   | 3/1997 | Olstein et al. |
| 5,672,515 | A |   | 9/1997 | Furlong |
| 5,813,403 | A |   | 9/1998 | Soller et al. |
| 6,073,037 | A |   | 6/2000 | Alam et al. |
| 6,584,060 | B1 | * | 6/2003 | Oohchida et al. ...... 369/112.05 |

OTHER PUBLICATIONS

"Method for Measuring a Physiologic Parameter Using a Preferred Site".

* cited by examiner

*Primary Examiner*—Monique T. Cole
(74) *Attorney, Agent, or Firm*—Barbara A. Wrigley; Oppenheimer Wolff & Donnelly LLP

(57) ABSTRACT

There is a need within the medical community for non-invasive instruments to measure critical physiologic parameters at the point of care. Such a technique may be applicable to a wide variety of commonly monitored physiologic parameters during critical care patient management. The invention is directed to a method of measuring the pH of a patient's tissue. The method includes measuring the optical signal from a specie whose fluorescence is pH sensitive, such as nicotinamide adenine dinucleotide (NADH) and also measuring the optical signal from a second biological marker, such as FAD, the fluorescence from the second marker being substantially insensitive to pH. The method includes determining the patient's pH by using the first and second optical signals.

28 Claims, 7 Drawing Sheets

NON-INVASIVE MEASUREMENT OF PH

FIELD OF THE INVENTION

The present invention is directed generally to medical devices and more particularly to non-invasive optical sensors for physiologic parameters.

BACKGROUND

Optical spectroscopy techniques have been developed for a wide variety of uses within the medical community. For example, pulse oximetry and capnography instruments are in widespread use at hospitals, both in the surgery suites and the post-op ICU's. These technologies have historically been based on absorption-based spectroscopy techniques and have typically been used as trend monitors in critical care environments where it is necessary to quickly determine if a patient's vital parameters are undergoing large physiologic changes. Given this operating environment, it has been acceptable for these devices to have somewhat relaxed precision and accuracy requirements, given the clinical need for real-time point-of-care data for patients in critical care situations.

Both pulse oximeters and capnography instruments can be labeled as non-invasive in that neither require penetrating the outer skin or tissue to make a measurement, nor do they require a blood or serum sample from the patient to custom calibrate the instrument to each individual patient. These instruments typically have pre-selected global calibration coefficients that have been determined from clinical trial results over a large patient population, and the results represent statistical averages over such variables as patient age, sex, race, and the like.

There is, however, a growing desire within the medical community for non-invasive instruments for use in such areas as the emergency room, critical care ICU's, and trauma centers where fast and accurate data are needed for patients in potentially life threatening situations. One such measurement needed in these environments is the blood and/or tissue pH level, which is a measure of the free hydrogen ion concentration. This is an important measure of intracellular metabolism. Biological processes within the human body require a narrow range of pH for normal function, and significant changes of pH from this range may be life threatening.

In addition to pH, it is also typical for other physiologic parameters such as the blood gases ($O_2$ & $CO_2$), blood electrolytes, cardiac-event enzyme markers, and other blood chemistry parameters such as glucose, to be measured and monitored during critical care treatment. Technologies for making these measurements have been in place for nearly fifty years in hospital laboratories. These measurements are made from blood samples drawn from the patient which are then sent to a laboratory for analysis. These laboratory measurements are typically made with electrochemical sensors.

Recent developments in non-invasive optical technology hold the potential that some of these measurements may be made at the point of care with sufficient precision and accuracy to carry out critical care monitoring and treatment. Also, there has been an increased interest in utilizing both the absorbance and fluorescence properties of naturally occurring biological molecules as physiologic markers for non-invasive optical measurements. Both of these techniques are complicated by the patient-to-patient variability in skin texture and chemical composition, both of which affect the optical properties of the skin and make universal calibration of such devices difficult.

SUMMARY OF THE INVENTION

Given the situation described above there is a need within the medical community for non-invasive instruments to measure critical physiologic parameters at the point of care. Such a technique may be applicable to a wide variety of commonly monitored physiologic parameters during critical care patient management.

One particular physiologic parameter that is important to monitor is the pH of a patient. One embodiment of a method of measuring pH includes measuring a first optical signal from a fluorescent biomolecule in a medium, the fluorescent biomolecule having a fluorescence characteristic that is pH sensitive. A second optical signal from a fluorescent marker in the medium is measured, the marker having a fluorescence characteristic that is substantially insensitive to pH. The pH of the medium is then determined using the first and second optical signals.

In one particular embodiment, the method includes measuring the fluorescent signal from nicotinamide adenine dinucleotide (NADH), which is dependent on the pH of the medium, and also measuring the fluorescence from flavin adenine dinucleotide (FAD), which is substantially independent of the pH of the medium.

Another embodiment of the invention is a system for measuring pH in a medium. The system includes a light source for optically exciting the medium, and a detection unit to detect a first optical signal from a fluorescent biomolecule in the medium whose fluorescence is dependent on the pH of the medium and to detect a second optical signal from a marker in the medium whose fluorescence is substantially independent of pH of the medium. A controller is coupled to receive detection signals from the detection unit related to the first and second optical signals and to determine the medium pH based on the first and second optical signals.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
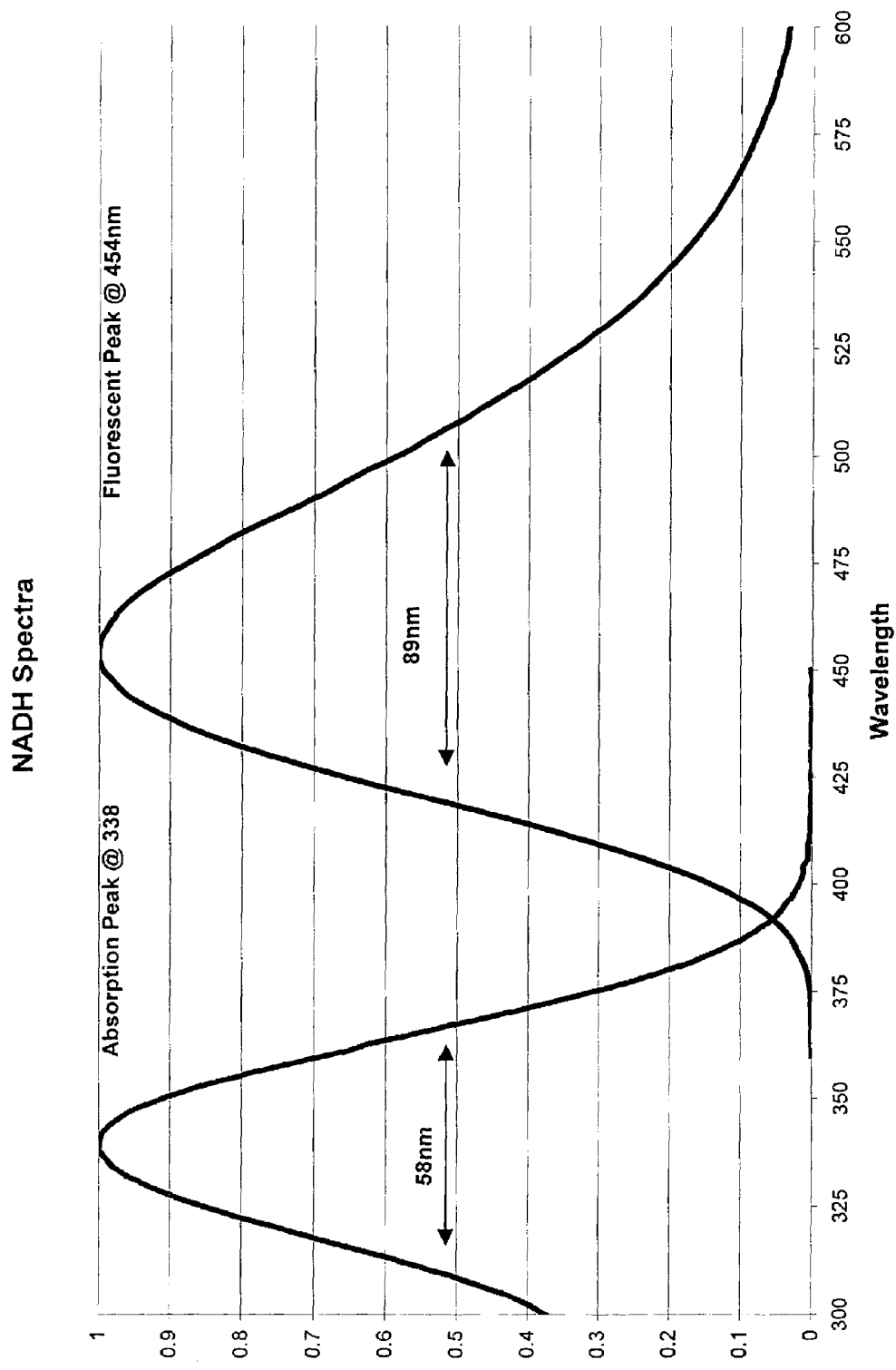
FIG. 1 shows normalized absorption and fluorescent emission spectra of a 0.06 milli-molar solution of nicotinamide adenine dinucleotide (NADH).

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is applicable to medical devices and is believed to be particularly useful for non-invasive optical physiologic sensors. Generally, the present invention relates to a method of measurement for performing non-invasive fluorescent spectroscopy on human tissue using naturally occurring biological markers. The measurements may be made with optical sensing devices in direct or near contact with the human tissue or in an in-vitro environment where blood or other bodily fluids or tissue are extracted for ex-vivo measurements. In addition to fluorescent spectroscopy, other optical measurement techniques such as absorbance spectroscopy or photon migration spectroscopy may be utilized separately or in conjunction with fluorescent measurement techniques. The sites may be accessed in a non-invasive manner without surgical procedures, providing the ability to both non-invasively calibrate and perform assay measurements at the same physiologic sites. Some suitable sites for performing non-invasive, optical measurements, based on the use of epithelial tissue, are described in U.S. patent application Ser. No. 10/195,005 titled, "Method For Measuring a Physiologic Parameter Using a Preferred Site", by inventors Victor Kimball, Steven Furlong, and Irvin Pierskalla, filed on even date herewith, which is incorporated herein by reference. Similarly, it may be beneficial in some cases to measure the additional physiologic parameters simultaneously with the main physiologic measurement, an example of this technique is described in U.S. Pat. No. 5,672,515 titled, "Simultaneous Dual Excitation/Single Emission Fluorescent Sensing Method For pH and $pCO_2$", by inventor Steven Furlong, which is incorporated herein by reference.

According to the method of the present invention, a first optical signal is obtained from a fluorescent biomolecule whose fluorescence is dependent on the pH of its environment. A second optical signal is obtained from a fluorescent marker whose fluorescence is substantially independent of the pH of the environment. The two optical signals may then be used to determine the pH of the environment where the biomolecule and the marker are located.

Two naturally occurring biological molecules which are of particular interest for physiologic monitoring are nicotinamide adenine dinucleotide ($NAD^+$) and flavin adenine dinucleotide (FAD). In particular, the reduced form of nicotinamide adenine dinucleotide (NADH) manifests a fluorescence spectrum that is pH dependent, while FAD has a fluorescence spectrum that is substantially independent of pH. The pairing of NADH and FAD may be useful for the non-invasive optical measurement of blood and/or tissue pH.

$NAD^+$ and NADH are converted into each other in many different metabolic reactions. NADH is used in the body to oxidize fats, sugars, and amino-acids into Adenosine Triphosphate (ATP) to form cellular bioenergy. From an optical spectroscopy point of view, NADH is the fluorescent form of the species, and chemical reactions that convert NADH to $NAD^+$ may be observed optically as fluorescence quenching at wavelengths associated with NADH emission.

One chemical reaction which converts NADH to $NAD^+$ is related to cellular respiration:

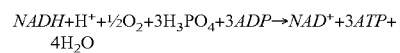
$$NADH+H^++\tfrac{1}{2}O_2+3H_3PO_4+3ADP \rightarrow NAD^++3ATP+4H_2O$$

where, in the presence of molecular oxygen, the reaction proceeds to the right as excess hydrogen ions ($H^+$) are introduced. In other words as the pH of the solution is decreased via the addition of hydrogen ions, NADH may be titrated into $NAD^+$ and the fluorescent emission from available NADH molecules is appropriately reduced. The addition of hydrogen ions is associated with a decrease in pH, since $pH=-Log[H^+]$.

A similar conversion of NADH to $NAD^+$ occurs in the so-called Krebs cycle, also sometimes referred to as the citric acid cycle. One such example is the oxidation of isocitric acid, which culminates in the final step shown below

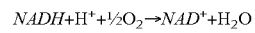
$$NADH+H^++\tfrac{1}{2}O_2 \rightarrow NAD^++H_2O$$

where again, in the presence of molecular oxygen, the reaction proceeds to the right as excess hydrogen ions ($H^+$) are introduced, in other words when the pH of the environment is reduced.

Both of the above chemical reactions suggest that NADH is useful as a naturally occurring biological marker for the non-invasive optical measurement of pH.

In addition to the above, flavin adenine dinucleotide (FAD) also plays a role in the citric acid cycle in the intermediate step outlined below

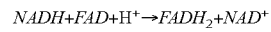
$$NADH+FAD+H^+ \rightarrow FADH_2+NAD^+$$

where FAD facilitates the conversion of NADH to $NAD^+$. Given this, the possibility that FAD enhances the sensitivity of NADH fluorescence to the local pH environment has been investigated. The enhancement may come about due to the presence of multiple pathways to convert NADH to $NAD^+$, which is observed experimentally as an increase in the change in NADH fluorescence per unit change in pH. The following experimental results outline the investigations into exploring this enhancement effect.

FIG. 1 shows the normalized absorption and fluorescent emission spectra of a 0.06 milli-molar solution of NADH (Sigma Aldrich Corp., St. Louis, part # N8129) diluted in $H_2O$. The spectra were collected using a SPEX FluoroLog 2 fluorometer with a spectral resolution of 1 nanometer (nm). This device was also used for all the other spectral measurements discussed below. FIG. 1 shows an absorption spectrum with an absorption peak near 338 nm, with a full-width half-maximum (FWHM) bandwidth of approximately 58 nm.

FIG. 1 also shows the fluorescent spectrum of the same NADH solution when excited near its absorption peak at 338 nm, the resulting fluorescent spectrum having an emission peak near 454 nm with a full-width half maximum of approximately 89 nm.

Figure 2:
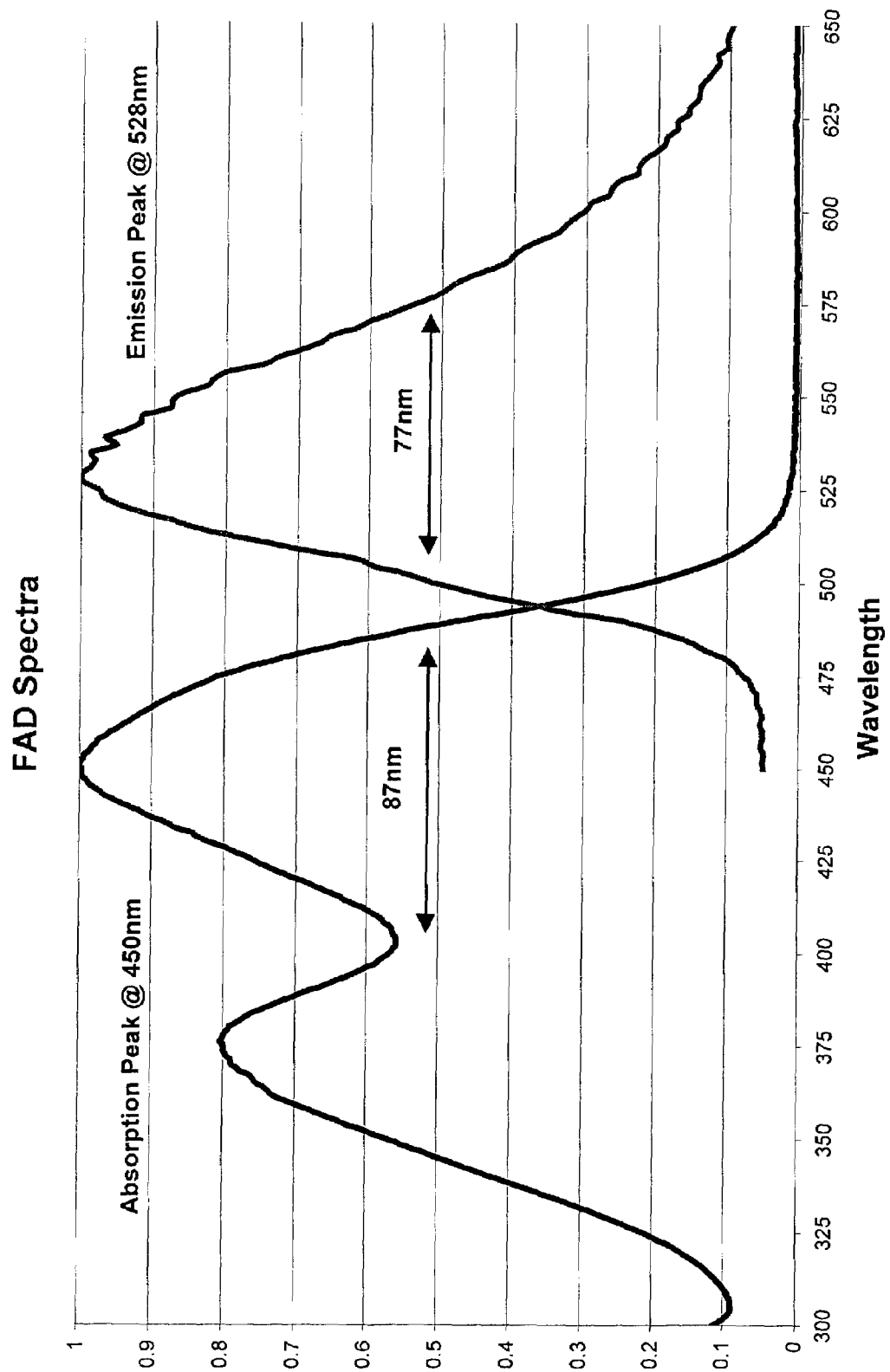
FIG. 2 shows normalized absorption and fluorescent emission spectra of a 0.14 milli-molar solution of flavin adenine dinucleotide (FAD).

FIG. 2 shows the normalized absorption and fluorescent emission spectra of a 0.14 milli-molar solution of FAD (Sigma Aldrich Corp., St. Louis, part # F6625) diluted in $H_2O$. The absorption spectrum has a bi-modal distribution with a short-wavelength regional absorption peak near 375 nm and a secondary maximum absorption peak near 450 nm with a full-width half maximum bandwidth of approximately 87 nm. FIG. 2 also shows the fluorescent spectrum of the same FAD solution when excited near its absorption peak at 450 nm, the resulting fluorescent spectrum having an emission peak near 528 nm with a full-width half maximum of approximately 77 nm.

Figure 3:
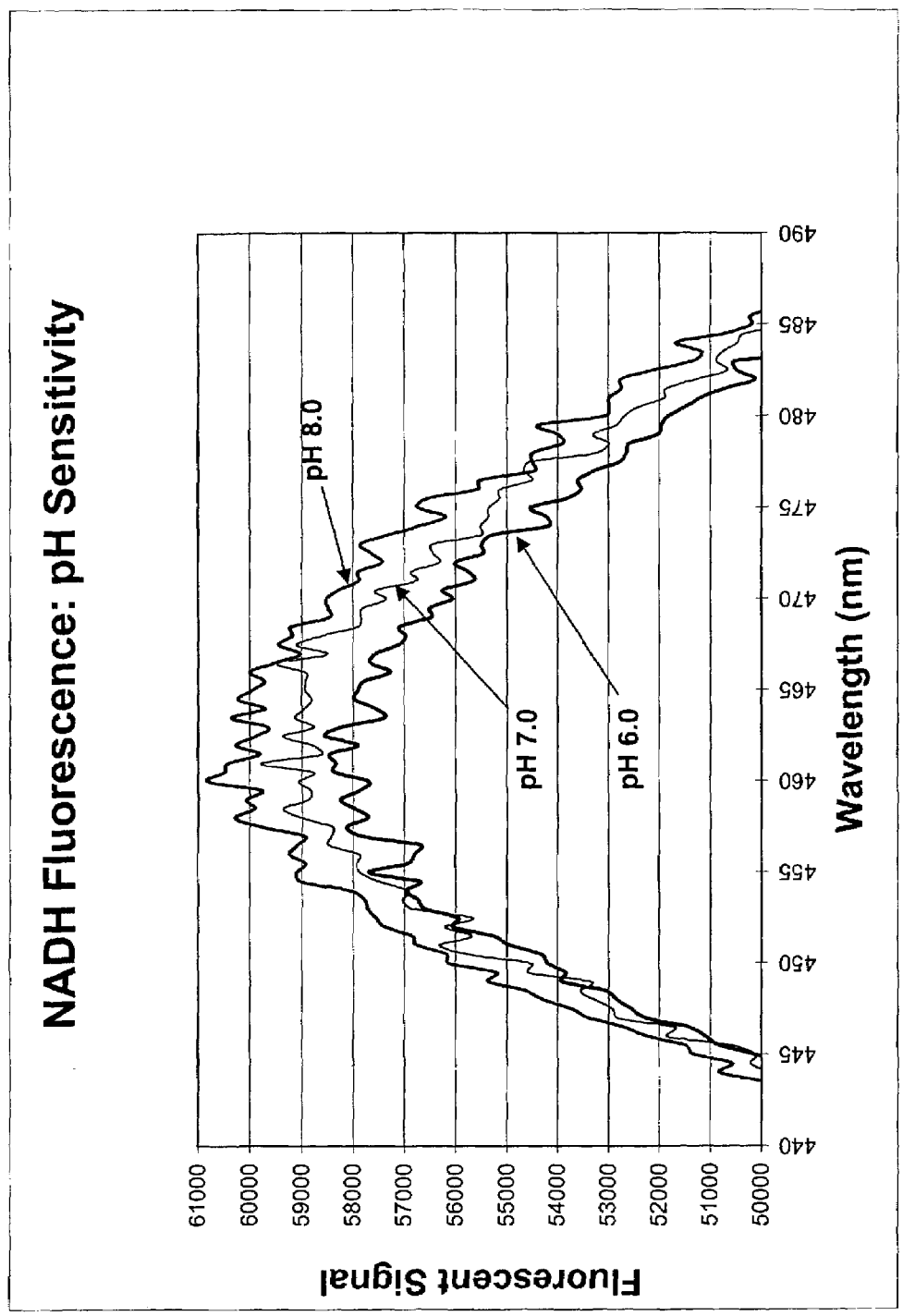
FIG. 3 shows fluorescent emission spectra for NADH over the pH range 6.0 to 8.0.

FIG. 3 presents three fluorescence curves obtained at different values of pH, showing the pH sensitivity of NADH fluorescence over the pH range 6.0 to 8.0. This range of pH brackets the normal human physiologic range of pH. Three separate NADH•$Na_2HPO_4$ (Sodium Phosphate)•$H_2O$ solutions with varying ratios of NADH to $Na_2HPO_4$ were prepared to achieve the desired pH values of pH=6, pH=7 and pH=8. The fluorescence was measured for each solution using an excitation wavelength near 360 nm.

The calculated results from this data set yielded a sensitivity of a 0.08% change in fluorescence intensity for a change in pH level of 50 milli-pH (0.050) units. It is useful to represent the results in this manner since many of the commercially available in-vitro pH sensors used in hospital emergency rooms and ICU's have precision and accuracy specifications in the 50 milli-pH range.

Figure 4:
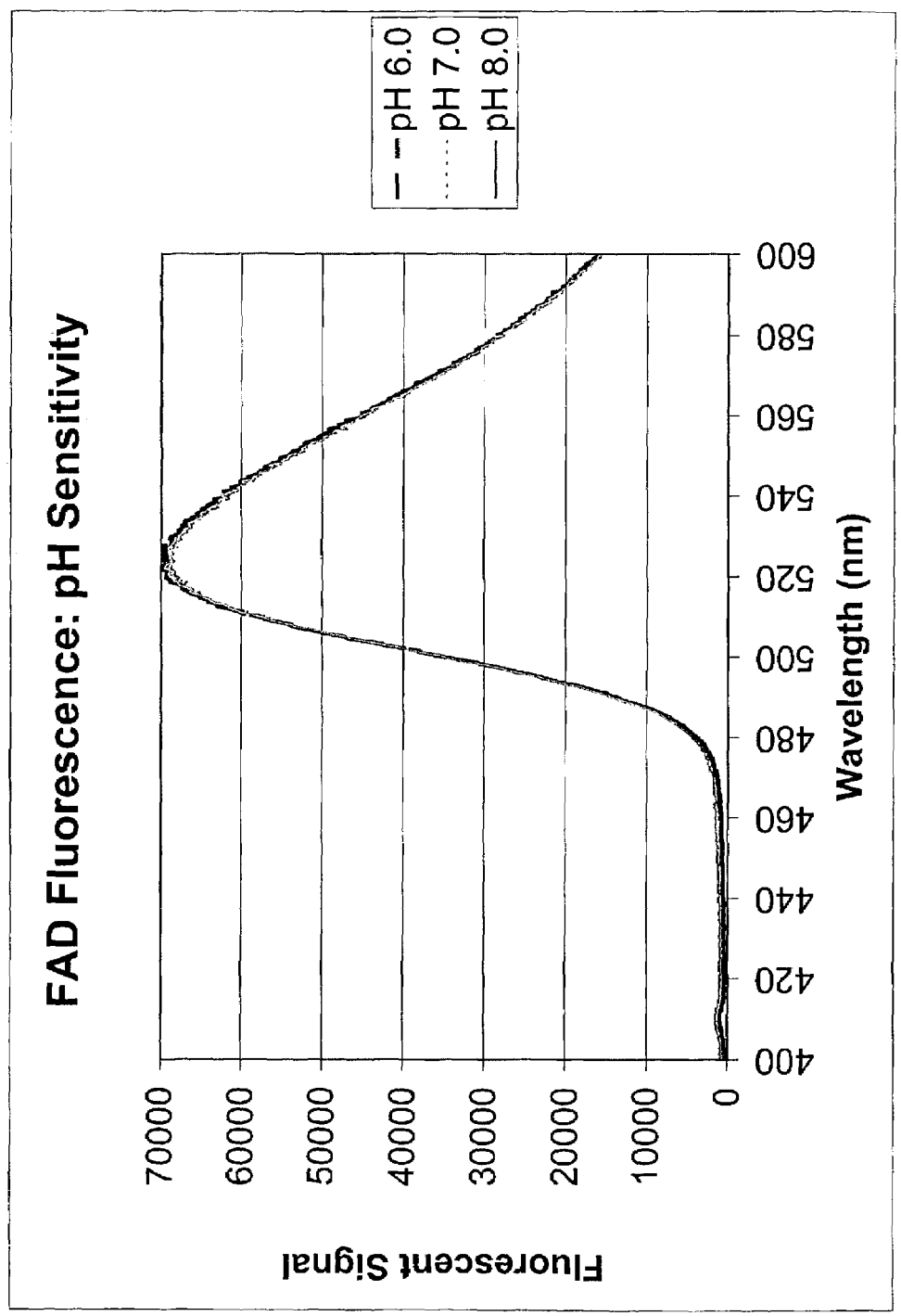
FIG. 4 shows fluorescent emission spectra for FAD over the pH range 6.0 to 8.0.

FIG. 4 presents three fluorescence curves obtained at different values of pH, showing the measured pH sensitivity of FAD fluorescence over the pH range 6.0 to 8.0. Three separate FAD•$Na_2HPO_4$ (Sodium Phosphate)•$H_2O$ solutions with varying ratios of FAD to $Na_2HPO_4$ were prepared to achieve the desired pH values of pH=6, pH=7 and pH=8. The fluorescence was measured with an excitation wavelength near 450 nm. The calculated results from this data set yielded a nearly indiscernible change in FAD fluorescence over the pH range of 6.0 to 8.0, a range which represents a one hundred-fold change in the hydrogen ion ($H^+$) concentration.

Figure 5:
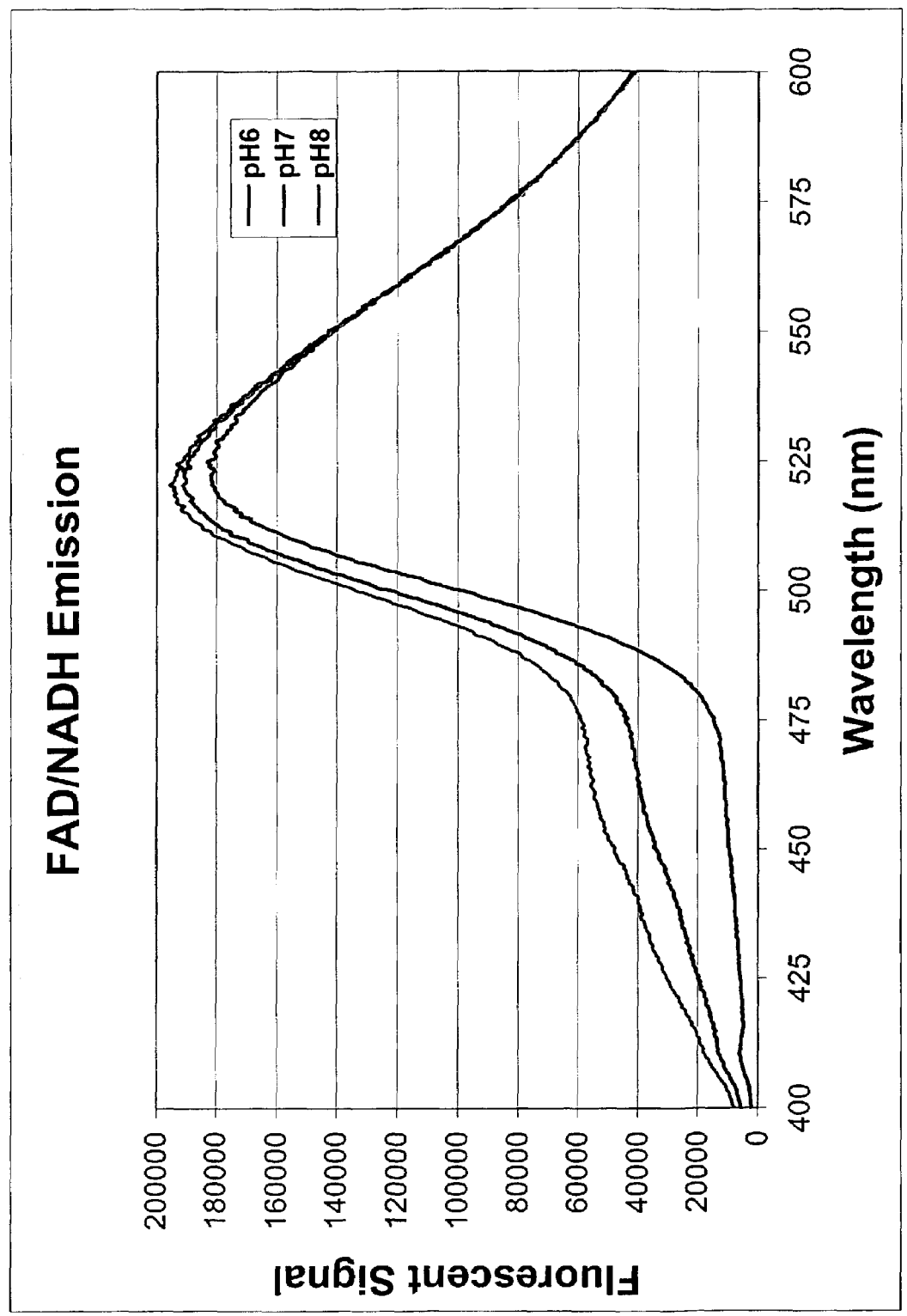
FIG. 5 shows fluorescent emission spectra for a blended mixture of NADH and FAD over the pH range 6.0 to 8.0.

FIG. 5 presents three fluorescence curves obtained at different values of pH, shows the measured pH sensitivity of the fluorescence of a blended mixture of NADH & FAD over the pH range 6.0 to 8.0. Three separate NADH•FAD•$Na_2HPO_4$ (Sodium Phosphate)•$H_2O$ solutions with varying ratios of NADH/FAD to $Na_2HPO_4$ were prepared to achieve the desired pH values of pH=6, pH=7 and pH=8. All 3 solutions were approximately 0.042 milli-molar for both NADH & FAD. The fluorescence was measured with an excitation wavelength near 370 nm. The excitation wavelength was selected to simultaneously excite both the NADH & FAD fluorescence. As can be seen in FIG. 1 and FIG. 2 both NADH and FAD have absorption bands with full-width half-maximums greater than 50 nm and with significant overlap. This allows for flexibility in the choice of the appropriate excitation wavelength for exciting both species with a common excitation band. This flexibility in the choice of excitation wavelength allows for the possibility of exciting more complicated spectroscopy systems in which more than two naturally occurring biomolecules have absorption bands falling in the same wavelength region. On the other hand, this flexibility may also allow for biasing the excitation band to a particular wavelength region to avoid exciting fluorescence from interfering species such as hemoglobin, collagen, elastin, or tryptophan.

Figure 6:
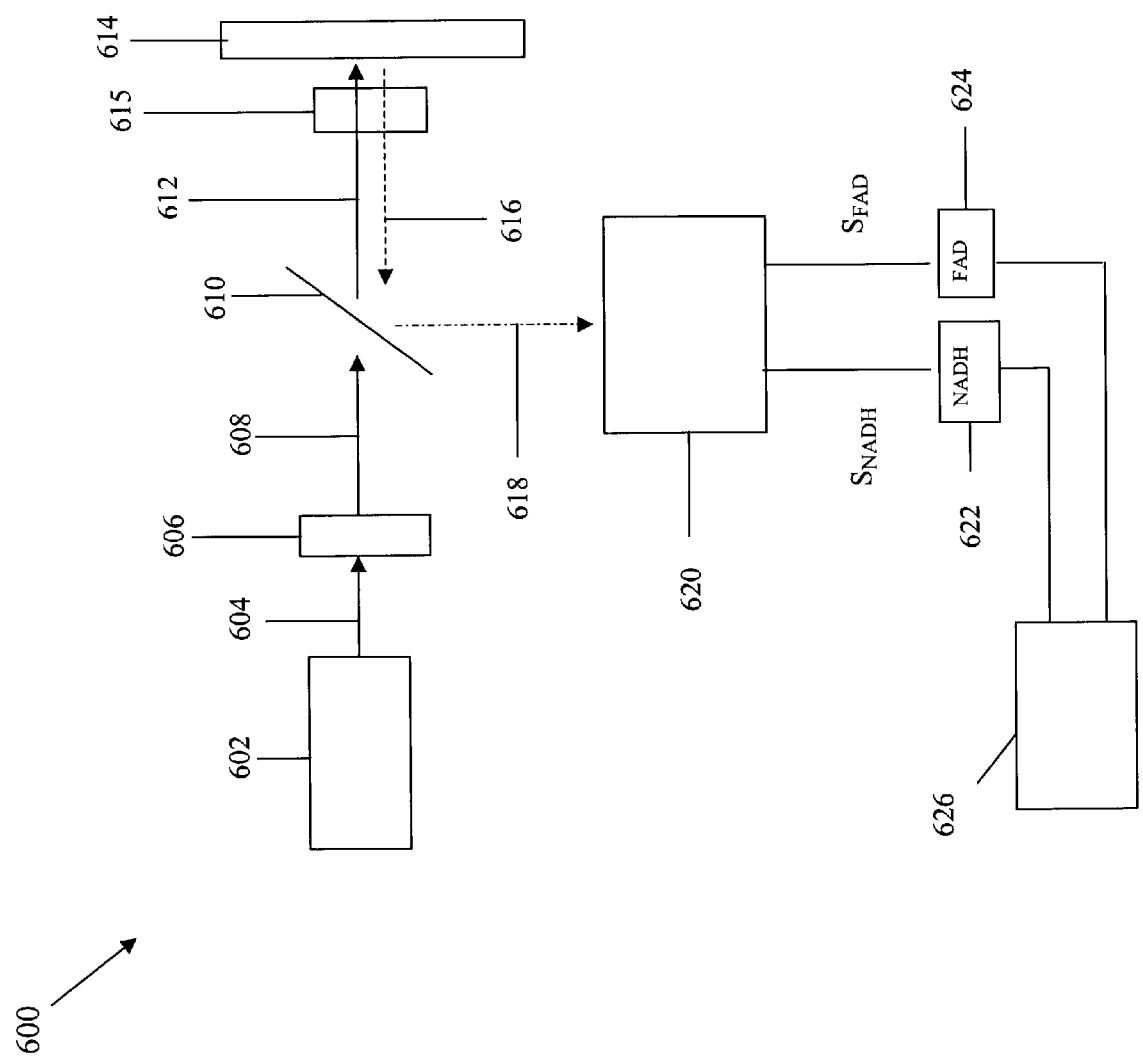
FIG. 6 schematically illustrates a system for measuring pH according to an embodiment of the present invention.

The curves show that the strength of the fluorescence signal in the region of about 425 nm–475 nm is very dependent on the value of the pH. In particular, the pH sensitivity at 450 nm (close to the peak of the NADH fluorescence) is approximately twenty times greater than for the solution of NADH alone, i.e. is approximately 1.6% per 50 milli-pH units. Narrow-band bandpass filters may be strategically placed in this wavelength region between about 425 nm–475 nm to avoid fluorescence from unwanted/interfering species which might otherwise corrupt the pH sensitivity. The fluorescence of the signal in the wavelength range 500 nm–600 nm is substantially less pH sensitive, particularly in the range of about 540 nm–600 nm. This wavelength range corresponds primarily to fluorescence from FAD. For wavelengths of about 560 nm and upwards, the fluorescence signal remains substantially pH insensitive. Thus, the signal in this wavelength region may be used as a stable reference signal. This stable, pH insensitive reference signal (from FAD fluorescence) in the region near 560 nm may also be used to augment alternative optical measurement techniques such as photon migration or absorption spectroscopy to determine pH. The broadband nature of the pH insensitive region at wavelengths near 560 nm and upwards, may allow for narrow-band bandpass filtering in this region at strategic wavelengths to avoid fluorescence from unwanted/interfering species which might otherwise corrupt the pH insensitivity. One particular embodiment of a non-invasive physiologic monitoring device 600 for measuring pH, based on the fluorescence from NADH/FAD, is depicted schematically in FIG. 6. A light source 602 emits optical radiation 604 which overlaps the absorption spectra of the naturally occurring fluorescent species used in the pH measurement. The light source 602 may emit narrow band radiation or may emit broadband radiation. Where the radiation is broadband, an optical bandpass filter 606 may be included to ensure only wavelengths in the desired wavelength range ultimately reach the medium 614 being probed. For example, where the fluorescent specie whose fluorescence is pH dependent is NADH and the marker whose fluorescence is largely independent of pH is FAD, the desired excitation wavelength range preferably lies under the absorption peaks of both NADH and FAD. Thus, for NADH/FAD, the excitation wavelength typically lies in the range 340 nm–380 nm.

The optical radiation 608 transmits through a dichroic filter 610, which is designed to pass wavelengths shorter than a pre-determined value and to reflect wavelengths longer than the pre-determined value. The optical radiation 612 is incident upon the medium 614 under test, via the patient interface 615, and a portion of the incident radiation is absorbed by NADH and FAD. The medium 614 may be the patient's tissue, for example epithelial tissue, although it may be other types of tissue, for example organ tissue. The medium 614 may also be a biological fluid, such as blood, serum or interstitial fluid. The medium 614 may be in vivo or in vitro.

Under illumination by the excitation light 612, the NADH and FAD fluoresce at their associated emission wavelengths and fluorescent radiation 616 emerges from the medium 614 as a superposition of NADH and FAD fluorescence. The fluorescent radiation 616 is reflected by the dichroic filter 610 as reflected beam 618 which is incident upon the wavelength detection and separating device 620. The wavelength detection and separating device 620 may be a wavelength dispersive device which separates the NADH fluorescent signal, $S_{NADH}$, from the superimposed FAD fluorescent signal, $S_{FAD}$. Detectors 622 and 624 are disposed to detect the signals $S_{NADH}$ and $S_{FAD}$, and are coupled to an analyzer/controller 626 that determines the pH of the medium 614.

The signals $S_{NADH}$ and $S_{FAD}$ may be ratio'd to form a pH dependent algebraic expression of the form $$R_{pH} = \frac{S_{NADH}}{S_{FAD}} \quad (1)$$

where the numerator term, $S_{NADH}$ is pH dependent and the denominator, $S_{FAD}$ may provide a stable reference signal to compensate for light source fluctuations or similar effects which would vary the amplitude of the excitation signal 612. The pH of the tissue may be calculated using the relationship for $R_{ph}$ shown above in equation 1.

The approach may also be applicable to in-vitro measurements, where in that case component 614 may be an optical cuvette filled with whole or diluted blood, blood serum or interstitial fluid.

It will be appreciated that various modifications and variations of the system 600 may be used. For example, the light 612 may be directed to the patient interface 615 via an optical fiber. Furthermore, the light 616 received from the medium 614 may pass along the same fiber that delivers the excitation light 612. In another embodiment, the signal light 616 may be transmitted to the separation unit 620 via a fiber separate from the fiber that delivers the excitation light, in which case the filter 610 may be omitted.

While the description of the system has so far been directed to the detection of fluorescence signals from the medium, the invention is not limited to the use of fluorescence signals. For example, the absorption of the NADH is also affected by the change in pH, and the optical signals detected by the device 600 may use absorbance signals related to one or both of NADH and FAD. In such a case, the light 608 typically includes light at two different wavelengths for absorption by NADH and FAD respectively. The different wavelengths may be obtained, for example, by tuning the filter 606, or may be obtained by tuning the light source 602 itself. Other approaches may also be used to obtain light at two different excitation wavelengths. The excitation wavelengths are typically selected so that the excitation light for absorption by NADH is not significantly absorbed by FAD and the excitation light for FAD is not significantly absorbed by NADH. For example the excitation wavelength for NADH may be around 300 nm while the excitation wavelength for FAD may be in the range 400 nm–500 nm.

Figure 7:
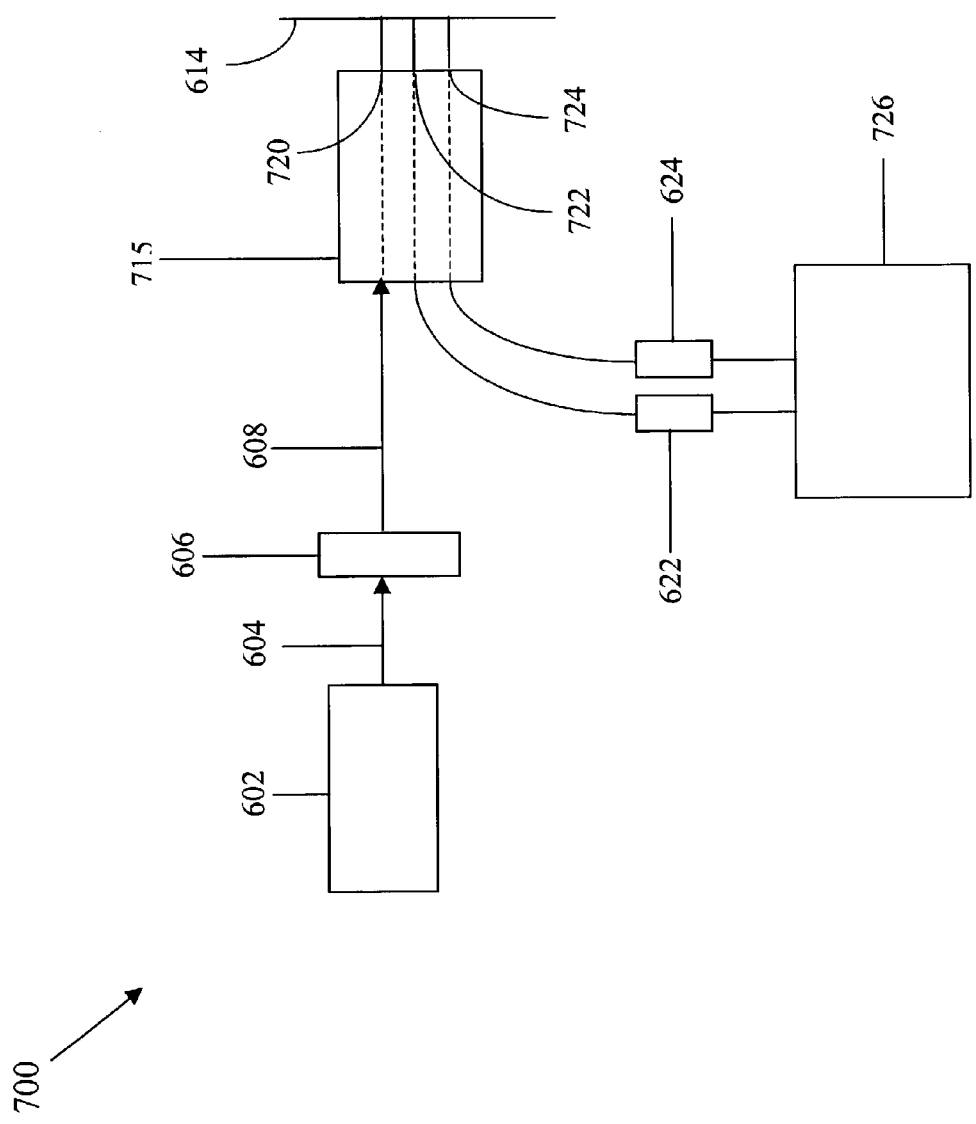
FIG. 7 schematically illustrates another system for measuring pH according to another embodiment of the present invention.

For absorbance measurements, the patient interface 715 typically includes an excitation port 720 to transmit the excitation light to the medium 614, and at least one detection port 722, displaced from the excitation port 720, to receive the light at scattered/absorbed light at the excitation wavelength, as is illustrated in FIG. 7. Preferably, the patient interface 715 includes at least two detection ports 722 and 724 spaced apart from the excitation port 720 by different distances. The difference in path length traveled by the excitation light to the first and second detection ports 722 and 724 from the excitation port 720 permits a more accurate estimation of the absorption of the excitation light in the medium. The detector 622 may be used to detect the signal received from the first detection port 722 while the detector 624 may be used to detect the signal from the second detection port 724. Additional detectors may also be used. The analyzer unit 726 determines the absorbance at one excitation wavelength from the signals measured on the detectors 622 and 624, and then at another excitation wavelength. The combination of the two absorbance signals may then be used to determine pH.

It will also be appreciated that, while the invention has been described in terms of using NADH and FAD, it is not intended that the invention be restricted to the use of these species. Instead, the invention is intended to cover the use of a first biological specie whose fluorescence is pH dependent and a second biological specie whose fluorescence is substantially insensitive to pH. By "substantially insensitive", it is meant that that pH-related variation in fluorescence of the marker is significantly smaller than that of the first biological specie, and that any variation in the fluorescence of the marker due to pH change is results in an error in the measured pH value that is smaller than the instrumental error resulting from, for example, noise, variation in light output from the source, etc.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A system for measuring pH in a medium, comprising:
a light source for optically exciting the medium;
a detection unit to detect a first optical signal from a fluorescent biomolecule in the medium whose fluorescence is dependent on the pH of the medium and to detect a second optical signal from a marker in the medium whose fluorescence is substantially independent of pH of the medium wherein the detection unit includes a wavelength light separator to separate light received from the medium into the first optical signal received from the fluorescent biomolecule and the second optical signal, and also includes respective first and second photodetectors to detect the first and second optical signals; and
a controller coupled to receive detection signals from the detection unit related to the first and second optical signals, the controller configured to determine the medium pH based on the first and second optical signals.

2. A system as recited in claim 1, further comprising a patient interface couplable to the medium, the patient interface including an excitation port for directing exciting light from the light source to the medium, and at least one detection port to receive light from the medium and direct the received light to the detection unit.

3. A system as recited in claim 2, wherein the detection unit detects fluorescent light from the fluorescent biomolecule.

4. A system as recited in claim 3, wherein the detection unit detects fluorescent light from the fluorescent biomolecule in the range of about 435–475 nm.

5. A system as recited in claim 2, wherein the detection unit detects fluorescent light from the marker.

6. A system as recited in claim 5, wherein the detection unit detects fluorescent light from the marker in the range of about 510 nm–600 nm.

7. A system as recited in claim 2, wherein the detection unit detects an absorbance signal for light absorbed by the fluorescent biomolecule.

8. A system as recited in claim 2, wherein the detection unit detects the absorbance signal for light in the range of about 330–390 nm.

9. A system as recited in claim 2, wherein the detection unit detects an absorbance signal for light absorbed by the marker.

10. A system as recited in claim 2, wherein the detection unit detects the absorbance signal for light in the range of about 340–405 nm.

11. A system as recited in claim 1, wherein the detection unit detects light from the fluorescence of NADH in the range 400 nm–500 nm.

12. A system as recited in claim 1, wherein the marker is FAD.

13. A system as recited in claim 12, wherein the detection unit detects light from the fluorescence of FAD in the range 500 nm–600 nm.

14. A system as recited in claim 1, wherein the controller determines the pH of the medium by calculating a ratio, $R=S_1/S_2$, where $S_1$ is a signal indicative of the first optical signal and $S_2$ is a signal indicative of the second optical signal, and also includes calculating pH of the medium using R.

15. A system for measuring pH in a medium, comprising:
a light source for optically exciting the medium;
a detection unit to detect a first optical signal from a fluorescent biomolecule in the medium whose fluorescence is dependent on the pH of the medium and to detect a second optical signal from a marker in the medium whose fluorescence is substantially independent of pH of the medium, wherein the detection unit includes a spectrally dependent path through a spectral scanning device to a photosensor, the spectral scanning device operative in a first configuration associated with the first optical signal from the fluorescent biomolecule and a second configuration associated with the second optical signal from the marker; and
a controller coupled to receive detection signals from the detection unit related to the first and second optical signals, the controller configured to determine the medium pH based on the first and second optical signals.

16. A system as recited in claim 15, further comprising a patient interface couplable to the medium, the patient interface including an excitation port for directing exciting light from the light source to the medium, and at least one detection port to receive light from the medium and direct the received light to the detection unit.

17. A system as recited in claim 16, wherein the detection unit detects fluorescent light from the fluorescent biomolecule.

18. A system as recited in claim 17, wherein the detection unit detects fluorescent light from the fluorescent biomolecule in the range of about 435–475 nm.

19. A system as recited in claim 16, wherein the detection unit detects fluorescent light from the marker.

20. A system as recited in claim 19, wherein the detection unit detects fluorescent light from the marker in the range of about 510 nm–600 nm.

21. A system as recited in claim 16, wherein the detection unit detects an absorbance signal for light absorbed by the fluorescent biomolecule.

22. A system as recited in claim 16, wherein the detection unit detects the absorbance signal for light in the range of about 330–390 nm.

23. A system as recited in claim 16, wherein the detection unit detects an absorbance signal for light absorbed by the marker.

24. A system as recited in claim 16, wherein the detection unit detects the absorbance signal for light in the range of about 340–405 nm.

25. A system as recited in claim 15, wherein the detection unit detects light from the fluorescence of NADH in the range 400 nm–500 nm.

26. A system as recited in claim 15, wherein the marker is FAD.

27. A system as recited in claim 26, wherein the detection unit detects light from the fluorescence of FAD in the range 500 nm–600 nm.

28. A system as recited in claim 15, wherein the controller determines the pH of the medium by calculating a ratio, $R=S_1/S_2$, where $S_1$ is a signal indicative of the first optical signal and $S_2$ is a signal indicative of the second optical signal, and calculates the pH of the medium using R.

* * * * *